United States Patent [19]
Buhler et al.

[11] Patent Number: 6,077,193
[45] Date of Patent: Jun. 20, 2000

[54] TRACKING SYSTEM FOR PROMOTING HEALTH FITNESS

[75] Inventors: Kirk A. Buhler, Corona; David R. Quam, Bellflower, both of Calif.

[73] Assignee: Unisen, Inc., Irvine, Calif.

[21] Appl. No.: 09/055,196

[22] Filed: Apr. 3, 1998

Related U.S. Application Data

[60] Provisional application No. 60/043,451, Apr. 10, 1997.

[51] Int. Cl.[7] ................................................. A63B 21/00
[52] U.S. Cl. ................................. 482/8; 482/1; 482/51; 482/901
[58] Field of Search ........................ 482/1–8, 51, 54–66, 482/900–903; 434/247, 257

[56] References Cited

U.S. PATENT DOCUMENTS

| | | |
|---|---|---|
| 4,708,337 | 11/1987 | Shyu . |
| 4,831,242 | 5/1989 | Englehardt et al. . |
| 4,842,266 | 6/1989 | Sweeney et al. . |
| 5,323,784 | 6/1994 | Shu . |
| 5,410,472 | 4/1995 | Anderson . |
| 5,591,104 | 1/1997 | Andrus et al. ............................... 482/1 |
| 5,890,997 | 4/1999 | Roth ............................................ 482/8 |

*Primary Examiner*—Glenn E. Richman
*Attorney, Agent, or Firm*—Knobbe, Martens, Olson & Bear, LLP

[57] ABSTRACT

This invention provides a system which allows users to personally create his or her own individual exercise program using any existing type of exercise machine, such as treadmills, bicycles, stair-climbers, weight lifting and the like. The invention provides a point-based incentive program to encourage the user to stay with an exercise program. Each user is supplied a personal data "key" on which is stored the individual's fitness program and on which is stored the person's progress in reaching or maintaining his or her fitness goal. The system provides a continuing incentive to the user to continue his or her exercise program by awarding points for: (i) time the user is on the machine; (ii) time the person indicates their heart rate is at a level that will allow the person to achieve their fitness goal; and/or (iii) time the person's measured heart rate is at a level that will allow the person to achieve his fitness goal. Each users key is personal and transportable so that users who travel can use their personal data key at any facility world-wide that has the data collectors installed.

20 Claims, 9 Drawing Sheets

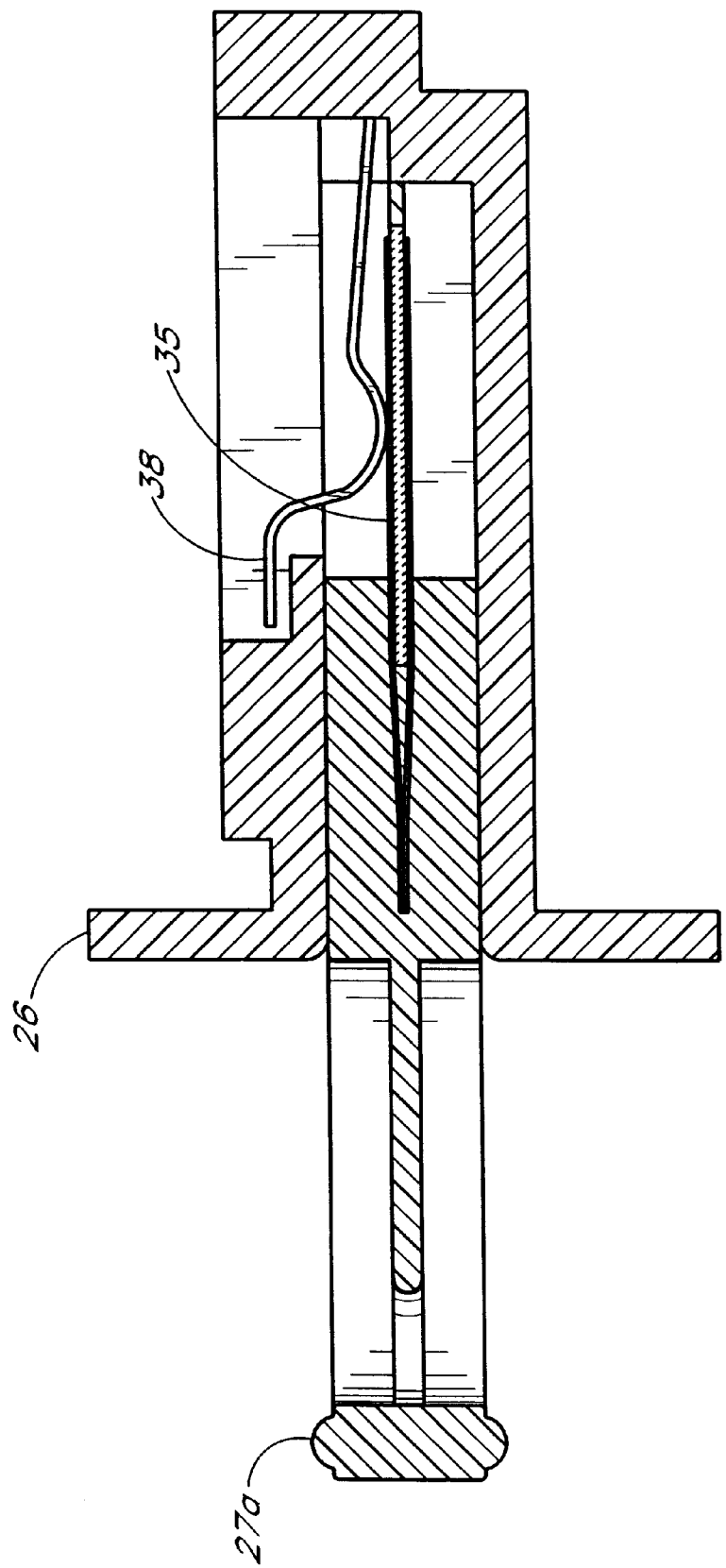

TRACKING SYSTEM FOR PROMOTING HEALTH FITNESS

RELATED APPLICATIONS

This application claims priority to U.S. Provisional Application Ser. No. 60/043,451 filed on Apr. 10, 1997.

BACKGROUND

1. Field of the Invention

This invention relates to a computer tracking system that assists and encourages the user to maintain or reach a fitness or personal goal.

2. Description of the Related Art

Although the advantages of a regular exercise program are widely publicized, the actual number of individuals engaged in such a program both in the U.S. and throughout the world is much less than the total population who would benefit from such a program. Reasons for this are many, but one common reason is that the user is personally uncomfortable about getting started in an exercise program or, even once started, the user drops out of an exercise program due to the lack of any personal incentive program.

SUMMARY OF THE INVENTION

This invention provides a system which both allows the user to personally create his or her own individual exercise program and provides a very simple, yet effective, incentive mechanism to cause the user to stay with an exercise program.

A significant feature of this system is that it is easily and conveniently installed on any existing type of exercise machine. Such machines includes treadmills, bicycles, stair-climbers, weight lifting and the like, and are located in a great many locations including fitness centers, gymnasiums, spas, and private homes.

Each user is supplied a personal data "key" on which is stored the individual's fitness program and on which is stored the person's progress in reaching or maintaining his or her fitness goal. The system provides a continuing incentive to the user to continue his or her exercise program by awarding points. In the preferred embodiment of this invention, these points are awarded in three ways.

1. A point is automatically awarded for every minute that the user's key is inserted at the data collector associated with an exercise machine.

2. A point is awarded for every minute the person indicates their heart rate is at a level that will allow the person to achieve their fitness level; and 3. A point is automatically awarded for every minute the person's heart rate is automatically detected at a level that will allow the person to achieve his fitness goal.

Because of the simplicity and relative low cost of this invention, data collectors can be installed for any conceivable exercise program or exercise device anywhere in the world. Thus, exercise rooms anywhere in the world on land and sea can easily and quickly install the system for the use of their patrons. Users who travel can use their personal data key at any facility world-wide that has the data collectors installed.

These and other features and advantages of the present invention will become readily apparent to those skilled in the art from the following detailed description of the preferred embodiments with reference to the accompanying drawings, the invention not being limited, however, to any particular disclosed embodiment.

BRIEF DESCRIPTION OF THE DRAWINGS

FIG. 9 is a cross-section of the data key and its receptacle in the data collector module.

DETAILED DESCRIPTION OF THE PREFERRED EMBODIMENT

Figure 1:
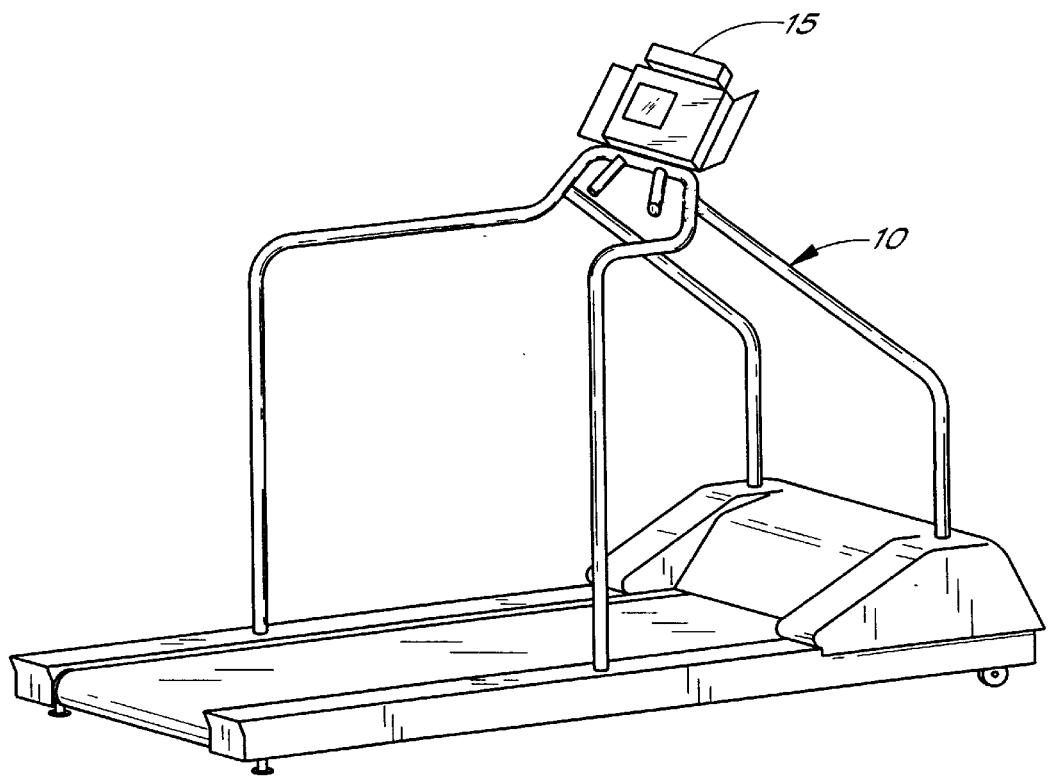
FIG. 1 is a perspective view of a treadmill exercise machine incorporating the invention.
Figure 2:
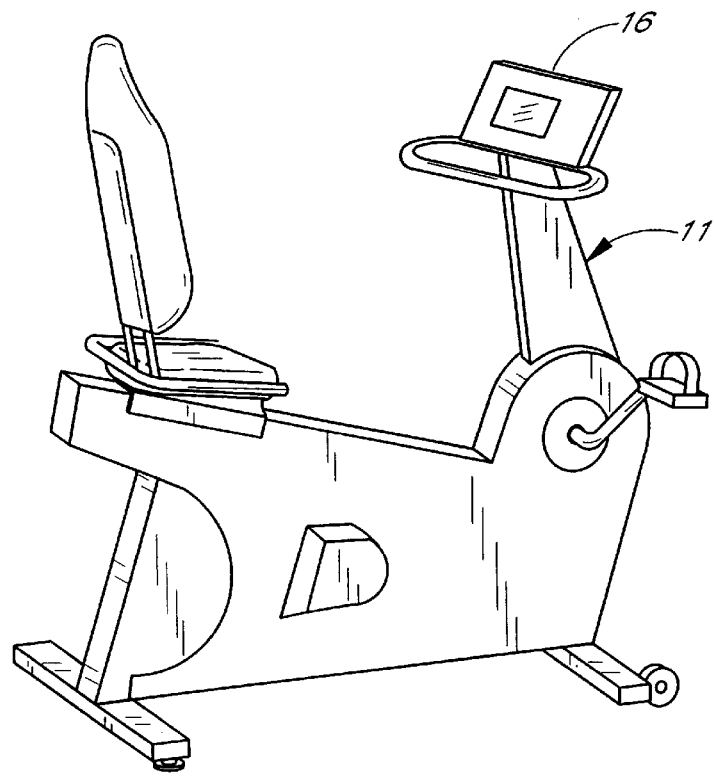
FIG. 2 is a perspective view of a bicycle exercise machine incorporating the invention.
Figure 3:
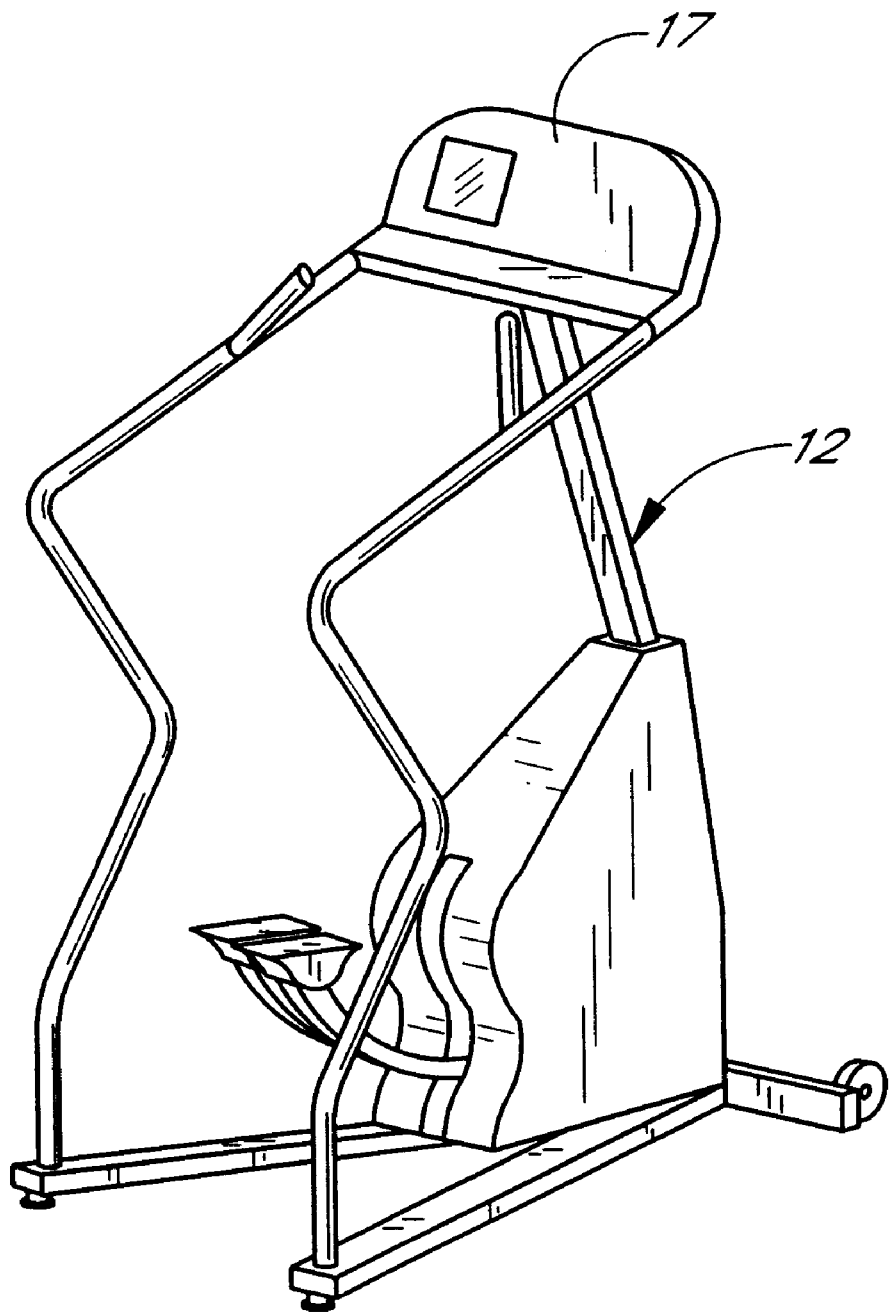
FIG. 3 is a perspective view of a stair climber exercise machine incorporating the invention.

FIGS. 1, 2 and 3, respectively, illustrate an exercise treadmill 10, exercise bicycle 11, and exercise stair climber 12. These, as well as other exercise machines, are in wide usage. Referring specifically to FIG. 1, the treadmill 10 includes an additional module, box or keybox 15 which operates as a data collector module and data readout and which, as described below, enables the user to continually collect "incentive points" to assist the user to follow and maintain a future program selected by the user.

FIGS. 2 and 3 illustrate alternative embodiments 16 and 17 of the data collector incorporated at the factory within the display of the exercise machine. A significant feature of the invention is that the data collector module 15 can be installed on any exercise machine in existence and can also be pre-installed at the factory during manufacture of the exercise machine.

Figure 4A:
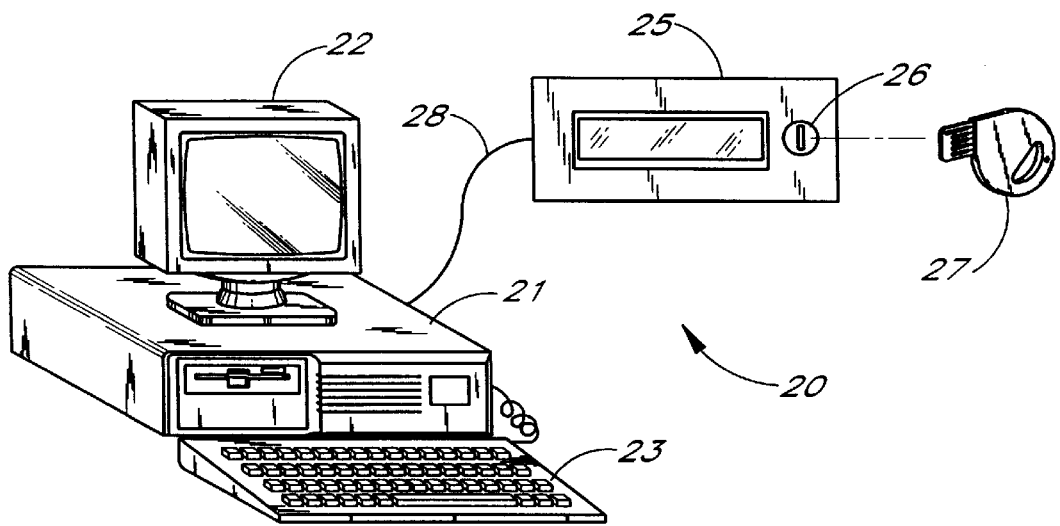
FIG. 4A illustrates a personal computer used within the system used to create the exercise program and store the program on a portable data key.
Figure 4B:
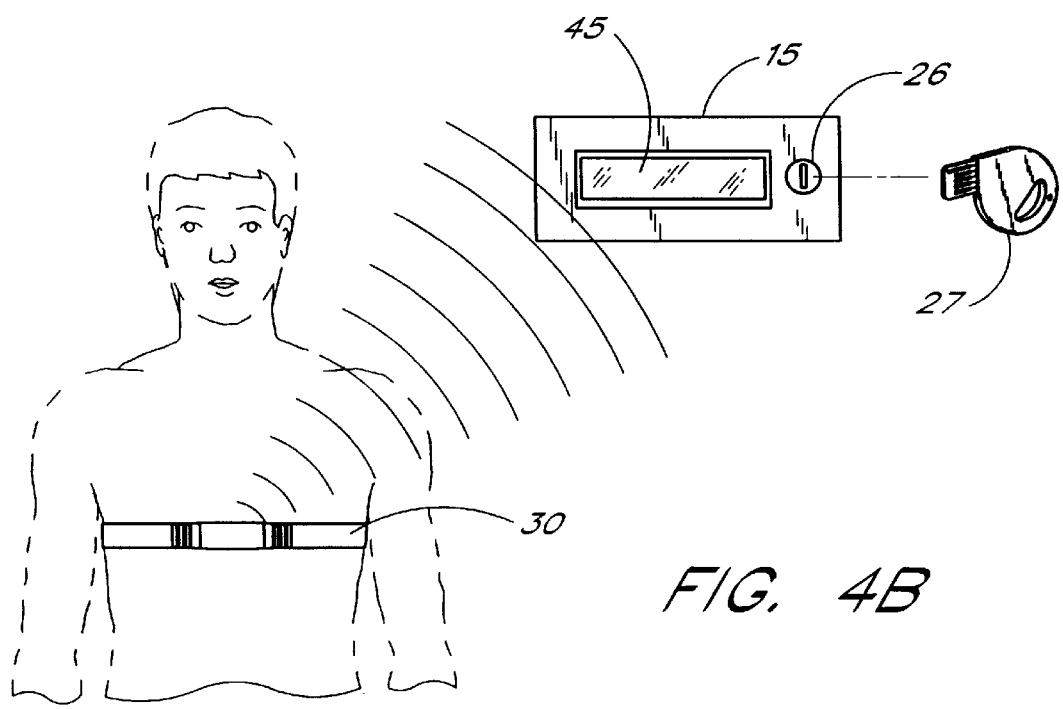
FIG. 4B illustrates the data collection module of the system installed in conjunction with the data key and heart rate detector and transmitter.

Referring now to FIGS. 4A and 4B, the overall system is shown with FIG. 4A illustrating the programming computer 20 and programmable data key 27 and FIG. 4B illustrating the data collector module and readout 15 and programmed data key 27.

The programming computer 20 advantageously includes a conventional personal computer 21, a touch screen and display monitor 22, and keyboard 23. The programming computer 20 further includes a key programming stage or box 25 having a receptacle or keyreader 26 for accepting the data storage key 27. Advantageously, key programming stage 25 also includes a conventional serial port for direct connection to the personal computer 21 via cord 28.

FIG. 4B illustrates the data collector and readout 15 associated with each exercise machine used within the system. As illustrated in FIGS. 5, 5A, 5B and 5C and described below, the same circuitry may be used in both unit 15 and in the key programming stage 25. Unit 15, however, physically resides on or proximity to an exercise machine as shown in FIG. 1. The unit 15 is responsive to entry of the key 27 into receptacle 26 and is also able to detect information transmitted through a wireless connection from a heart rate detector belt 30 or the like worn by the user. The unit 15 includes a readout display 45.

Figure 6:
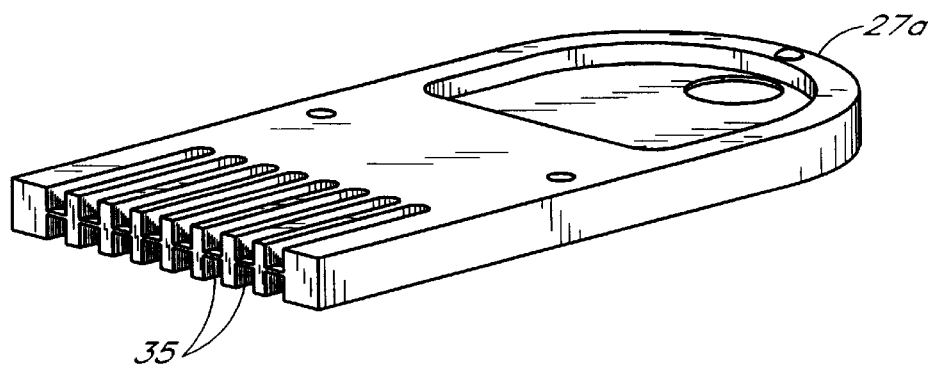
FIG. 6 is an enlarged view of one embodiment of the data key.
Figure 7:
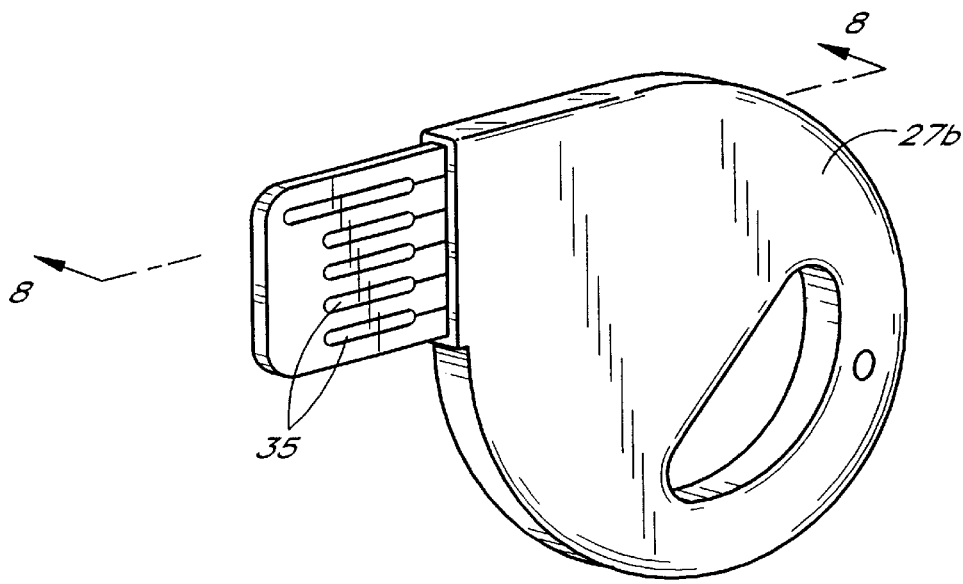
FIG. 7 is an enlarged view of another embodiment of the data key.
Figure 8:
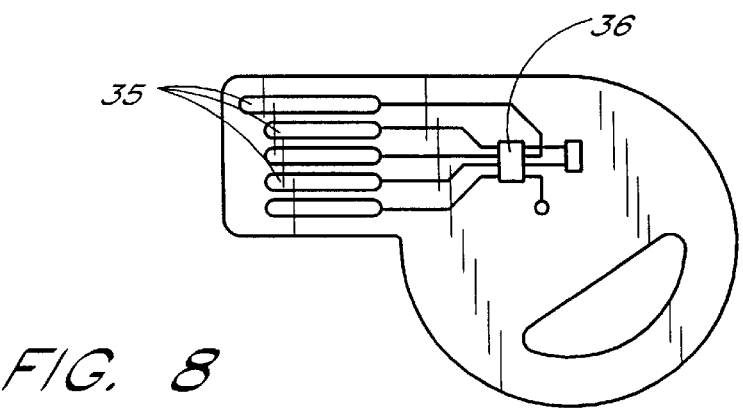
FIG. 8 is a cutaway view of FIG. 8.

Two embodiments of the data storage key 27a and 27b are shown in FIGS. 6 and 7. These keys are shown much enlarged. In the preferred embodiment, the actual key 27a is typically 1¼ inches long, ¾ inches wide and ⅛ inches thick. As shown in the cross-sectional view of FIG. 8, each key 27 includes a plurality of electrical contacts 35 connected to an EEPROM 36 which functions as a re-programmable memory storage for keeping track of the exercise performed by the user and awarding points to the user. The cross-sectional view of FIG. 9 illustrates the manner in which contacts 35 of key 27a engage contacts 38 within the receptacle or keyreader 26.

Figures 5, 5D:
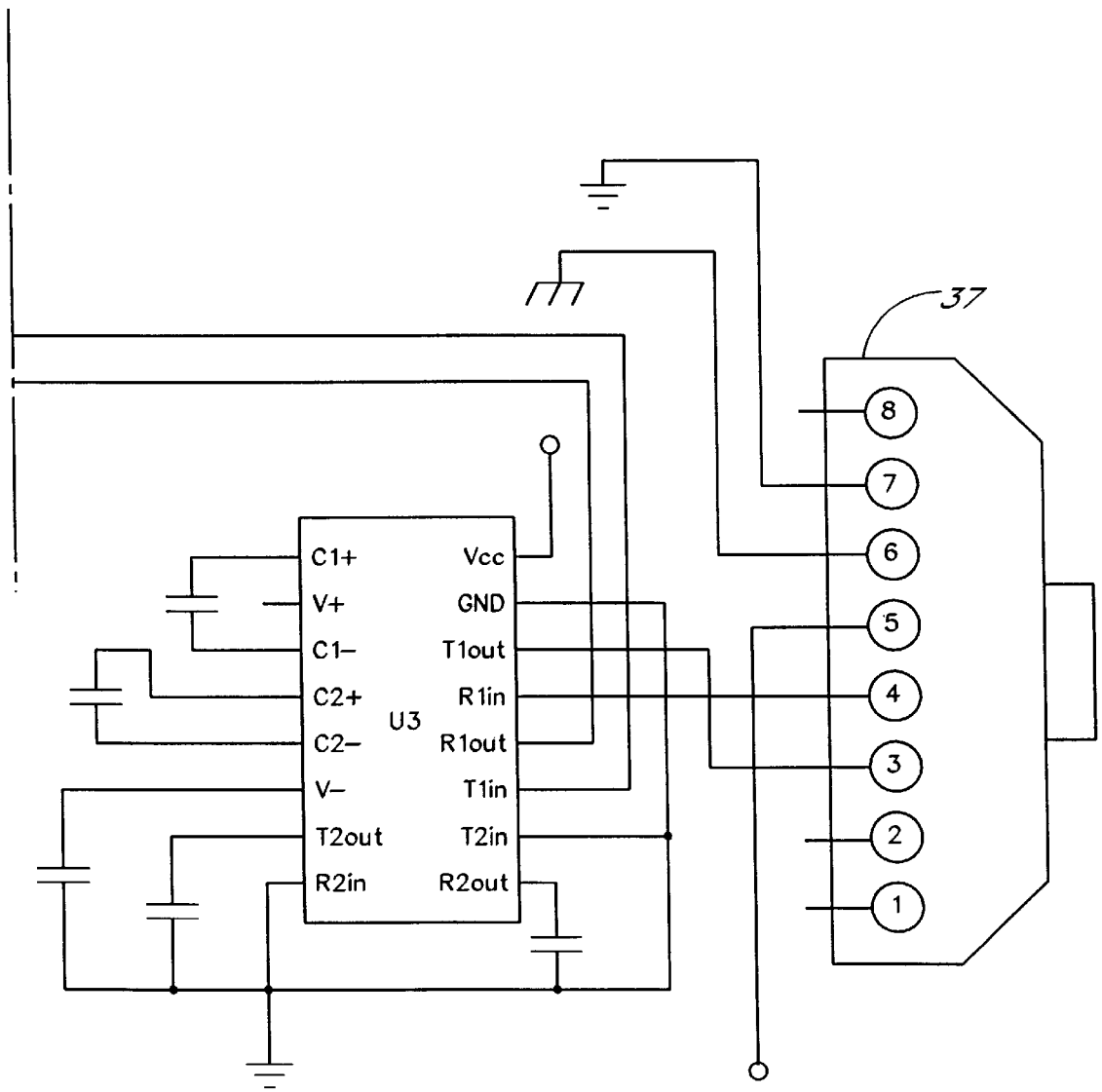
FIGS. 5, 5A, 5B, 5C, and 5D illustrate a circuit schematic of the system for programming the data key, for recognizing the information stored in the key, and for updating the information stored on the data key.
Figure 5A:
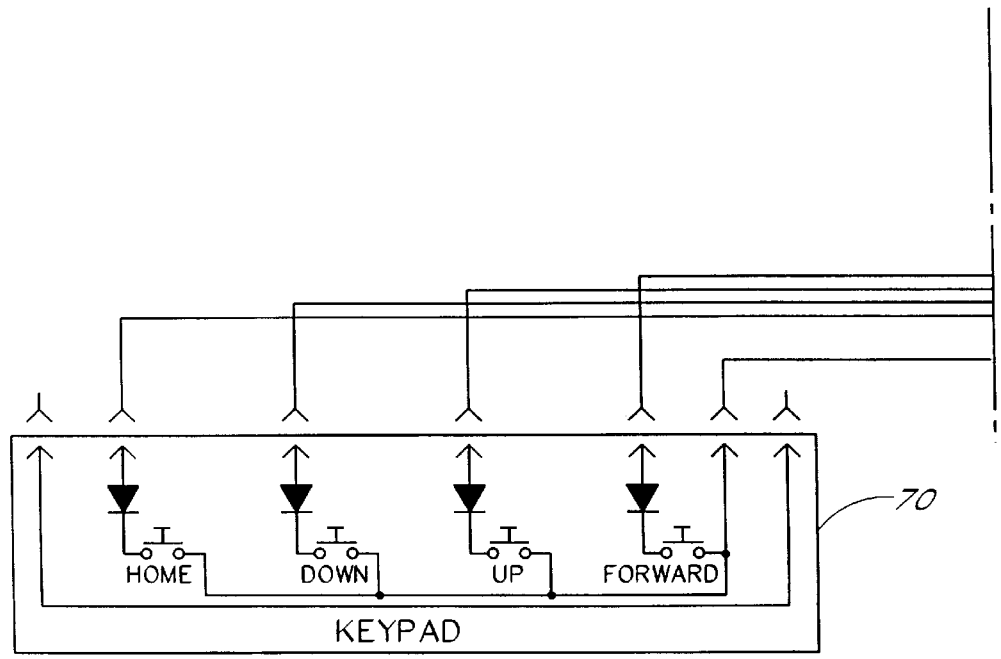
Figure 5B:
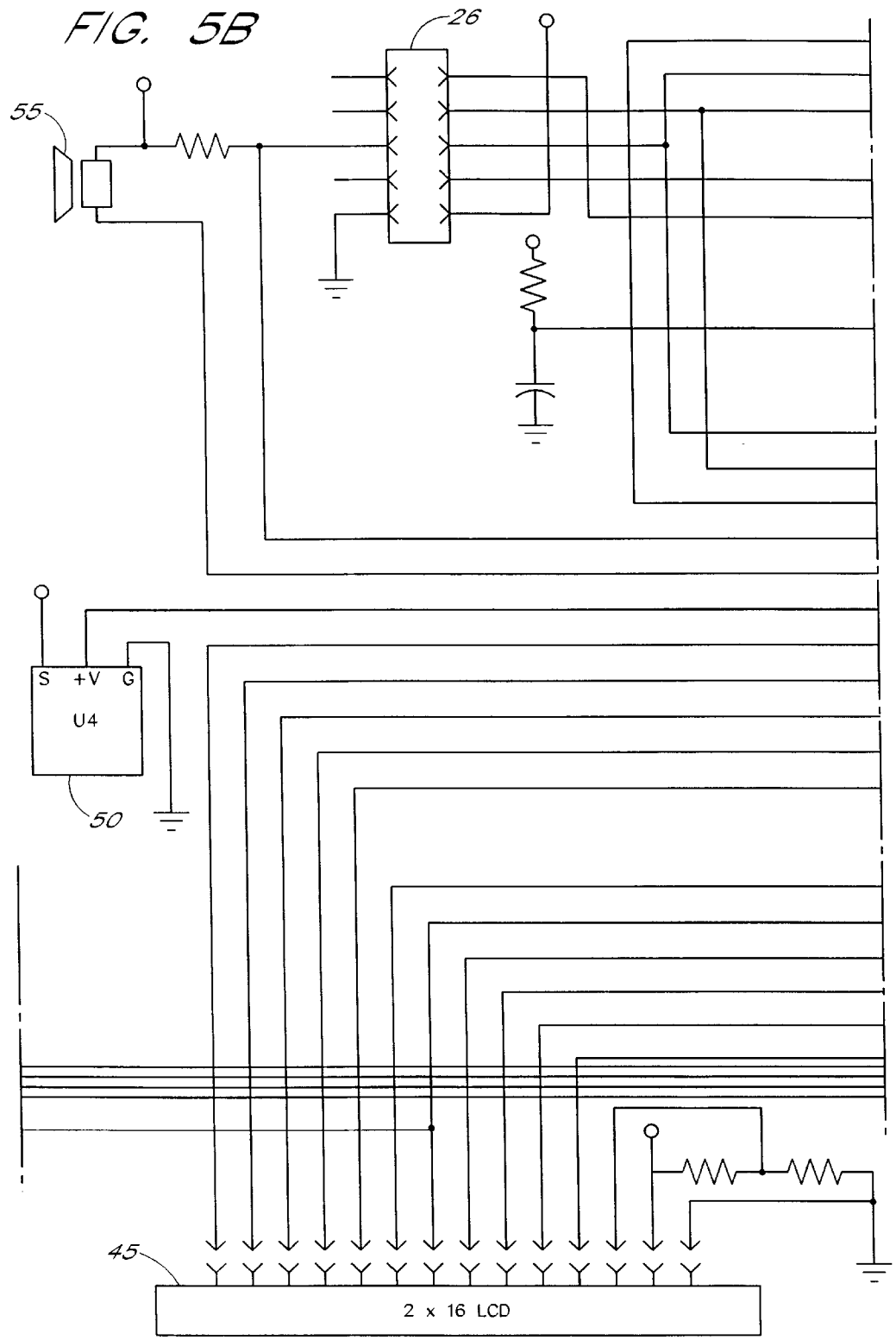
Figure 5C:
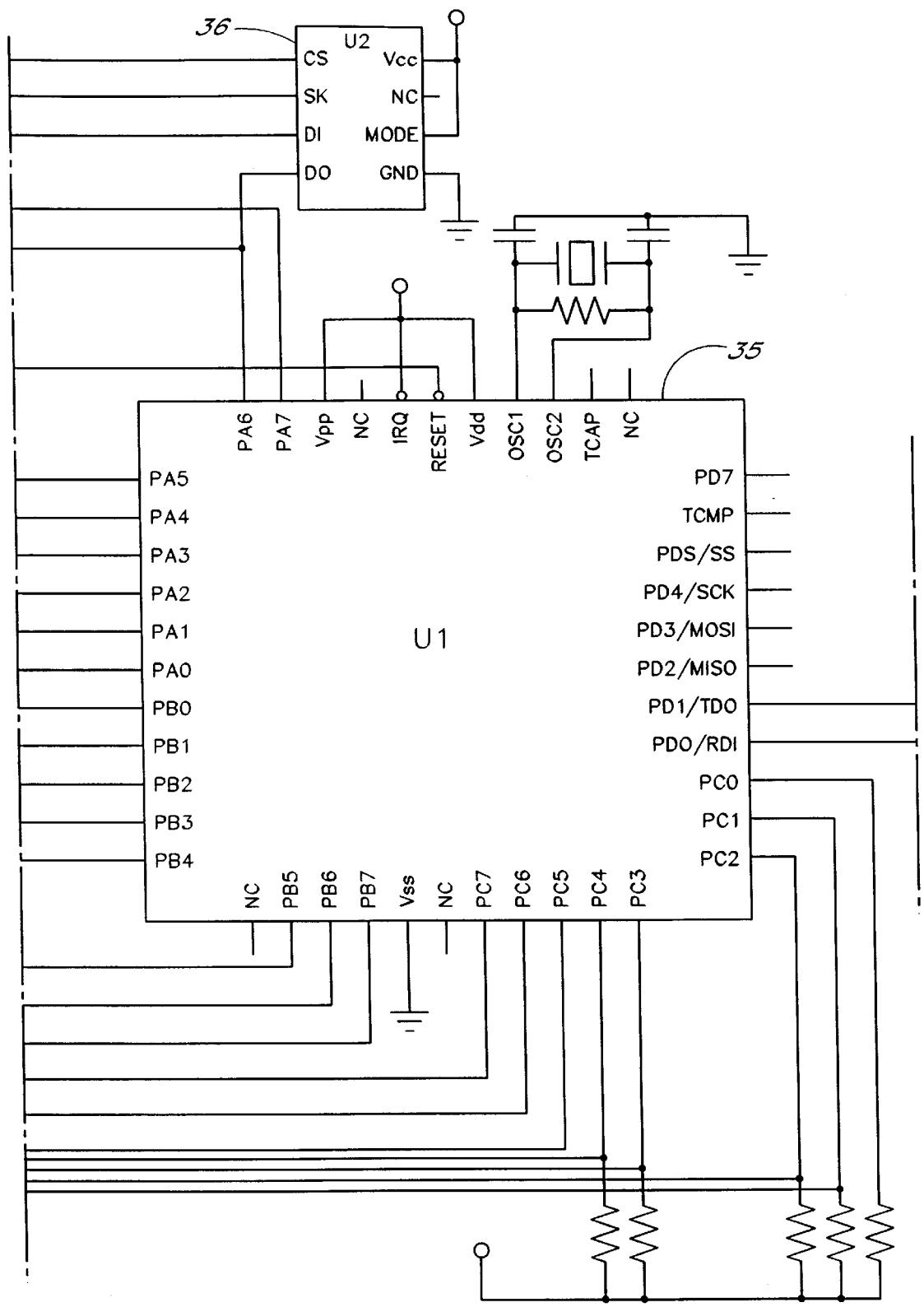

The following is a detailed description of the function of the software within the units shown in FIGS. 4A and 4B, including reference to the module circuitry illustrated in FIGS. 5a, 5b and 5c. Appendix C, which is included as part of this invention specification, describes in detail the software used in the personal computer 21. Appendix D, included as part of this invention specification, is the source code for the software used in the micro-controller of units 15 and key programming stage 25. Appendix E, included as part of this invention, describes the memory map of the data key 27.

For facilitating understanding of the overall system and its capabilities, the system is described as it would typically be installed and used in a fitness center. It will be apparent, however, that the computer tracking system of this invention has wide utility over a wide range from a single user's home to the most sophisticated fitness center.

The Programming Computer 20

With no key 27 inserted into the key receptacle 26 and no menu option chosen, the monitor 22 displays the general welcome screen, and tells the user to insert his/her key.

The system and software provides a number of menu options. If "Default options" is chosen, a trainer at the fitness center customizes the system. If "Reports" is chosen, a number of reports may be selected, including sorting by a field. If "Timer key" is selected, the trainer may program the key used for setting the correct time for all the auxiliary keyboxes. If "Help" is chosen, a number of help screens will come up.

When a key 27 is inserted into the receptacle 26 of module or box 25 connected to the programming computer 20 (FIG. 4A), the computer 20 attempts to read the data on the key. Based on this, the computer decides whether the key is (1) new, (2) an existing user, or (3) unusable.

If the key is unusable, the computer displays an error, and tells the user to remove their key and see the fitness staff. Then it goes back to the main welcome screen.

Fitness Staff Key

If the key 27 represents the fitness staff, an administration menu pops up. This menu gives the fitness staff the option to configure the system, and print out various reports (see below). When the fitness staff is done, he/she is told to remove their key, and the welcome screen comes back up.

New Key

If the key 27 is new, the program assumes that a new user should be initialized onto the system. A number of steps are taken here. First, the user's profile data is entered. If the club requires it, a PAR-Q test is then done, and if the user is deemed a health risk, they are told to remove their key from the keybox, and to see the fitness staff.

Next, the club may require a fitness test. If not, the user can conduct such a test. The user is told to remove their key, do the fitness test, and come back with the results. A typical fitness test is a 12-minute assessment on an exercise machine such as the treadmill 20 or bicycle 11 where the user is given 12 minutes to cover as much distance as possible. The user then re-inserts the key and enters the number of miles completed during the fitness test, after which the computer program calculates a fitness level or category based upon the user's age, sex, and distance covered.

If no fitness test was required, a fitness level (number of miles) is entered directly. Once a fitness level is in the system, a number of user goals are offered. The user (with the possible help of the fitness staff) chooses one of these goals. Next, a number of exercise programs are offered based on this information. The computer originally defaults to the most likely program based on the fitness level and goal, but the user (with the possible help of the fitness staff) may choose a different program. Users at levels 1–2 may choose programs 1–4. Other users may choose any program. After the program is chosen, the computer tells the user what this program will entail and the requisite number of points that the user needs to accumulate to accomplish the selected fitness program. The user (or fitness staff) may modify the chosen program to a certain extent. Once this is done, the program is entered into the main database, along with any other relevant information. The user's key is then initialized. The user is given the option to have their exercise program printed out. Finally, the user is told to remove their key 27, and begins their exercise program. Then the main welcome screen comes back up.

Existing User Key

If the key 27 represents an existing user (but not the fitness staff), the programming computer 20 checks to see if an exercise program is in effect for this user. If not, a program is selected as noted above. Either way, all data is then read off the key 27. The user's database information is now retrieved. The new data is totaled into the existing data, stored back into the database, and the exercise data on the key is cleared. If the user has reached their goal, the user is congratulated, and told to see the fitness staff for the next step. Then the user is informed of their new status, including a brief exercise history. The user is given the option of printing out a detailed or summarized exercise history. Finally, they are told to remove their key, and the main welcome screen comes back up.

The Data Collector Unit 15

The program resides inside the keyboxes 15 associated with each piece of exercise equipment. While no key 27 is detected, a welcome screen is displayed on display 31.

Once a user inserts key 27 into the keyreader receptacle 26, the keybox 15 attempts to read the key's data. If the key is unusable, an error message is given, and the user is instructed to remove their key and see the fitness staff. If the key is full, the user is told to remove the key and insert it into the main computer, so the key data can be read and cleared.

Otherwise, the keybox 15 greets the user and tells them their current status. This consists of displaying (1) their fitness level and exercise program name, (2) the number of points accumulated so far, (3) the number of points in their final goal, (4) the number of points needed today, and (5) the heart rate range necessary during exercise. These items are shown for a few seconds each. Then, the user is instructed to start exercising. As their exercise, new points earned are automatically written to the key 27, and the user's ongoing status is shown on the screen. This ongoing status consisted of repeatedly displaying (1) the elapsed time in the form of dashes, (2) their heart rate, (3) new points earned so far, and (4) their heart rate, including a warning if their heart rate is out of range. When the daily goal has been achieved, i.e., the user has accumulated the number of points needed to reach his goals the keybox tells the user to go through the cool-down period (if any). Then the keybox 15 informs the user that the daily goal has been achieved and the user is instructed to remove the key.

1. Overall Operation

The box 15 has five basic functions: time keeping, displaying information and prompts, heart rate detection, sound to indicate various events, reading the user's key, and awarding points. An additional function is available when the device is connected to a serial port on a personal computer 21 (see FIG. 4A). When the device is connected to a serial port, the unit is capable of testing all functions, transferring internal memory and memory stored on a key 27, and saving data to both its internal memory and a key 27.

1.1 Time Keeping

Each unit 15 contains a micro-controller 35 (FIG. 5C) that has time keeping capability. The unit keeps track of seconds, minutes, hours, days, months, and years. When the day changes, the box saves the new date. One specific configuration of the invention uses a 4 Megahertz clock or resonator 36. This option is used when the unit is used with the serial port 37 as part of the key programming stage 25. Baud rate is 2400 for this configuration. These units are capable of being used as data collectors 15, but draw a higher current during operation. The accuracy for this version is less then 0.3% or about 1 day each year. A possibility is for a 4.8 Hour accuracy with tuning each box and crystal or resonator.

The second configuration, advantageously used with boxes 15, uses a lower current 500 Kilohertz clock or resonator. Baud rate is 300 for this configuration. The accuracy for this version is less than 0.3% or about day each year. A possibility is for a 4.8 Hour accuracy with tuning each box and crystal or resonator.

1.1.1 Manual Time Setting

Manual time setting can be performed when the power is applied to the unit 15. The initial time and date is set at the factory. When the unit is in operation, it will save a new time and date when the day changes.

1.1.2 Unit 15

The time and date on a time setting key 40 can be set externally without pressing and keys at the programming computer stage 25. The key 40 has a "t" placed in memory location #13 or OD. When a key 40 with this configuration is placed into a unit 15, the unit 15 will adopt the time and date placed on the key. The key 40 itself does not track the time, it holds the time that was stored on it by the programming computer 25. In this mode of operation, a key 40 can be placed into the programming computer stage 25, and removed in about a second. This does not indicate that the time and date on the key is correct, but that the unit 15 will accept the time and date on the key. The time and date on the key is not changed, and the key can be moved from unit 15 to unit 15 to update the time and date on all units within a fitness center. This is useful when the time and date on the unit 15 is in question, or when a time or time zone has occurred. The accuracy of the time will be the amount of time it takes from removing the key from the programming computer 25 to when the key is placed in the unit 15.

1.2 Display 45

The display 45 (FIG. 5B) uses a two line by 16 character display 45. The display is capable of showing a variety of information. The box 15 operates in two modes: a set-up/ diagnostics mode and an operation mode. In the set-up/ diagnostics mode, the information being displayed is established by the manufacturer, and is described in the Set-up/ Diagnostics Screens section. A total of 16 different user screens display information to the user as the box is being used. These screens are shown in the Operations Screen section. The use of each of these screens is described in detail in the Box Operation User Section. The English screen and the translations for each screen is located in Appendix B.

1.3 Heart Rate Detection

Each box 15 is equipped with either a Polar Heart Rate receiver 50 (FIG. 5B) or a Cardio Sport Heart Rate monitor (not shown). The box uses a 6 beat rolling average for heart beat. In addition to the averaging, three filters help to reduce poor heart rate readings. The first filter will not accept two heart beats if they occur too close together. The second filter cancels variations in the users heart rate that exceed 10 BPM on two consecutive beats. The third filter masks all values outside 50 to 200 BPM reading.

1.4 Keypad

The keypad 70 (FIG. 5A) includes four keys, two shown, and two hidden. The HOME/YES key currently has no function in the use mode, but in the set-up mode, increases the changeable location. The FORWARD/NO key currently has in the use mode, but in the set-up mode, moves to the next changeable location.

1.5 Keyreader 26

The keyreader receptacle 26 (FIG. 5D) itself has five possible contacts 38 on each side. The contacts are configured such that if the key 27 is inserted backwards, it is not detected by the system. The key is designed to connect to a 10-pin (2×5 contact) card edge connector. For a description of the data and format stored on the key, refer to the key specifications.

The contacts on the connector is configured as follows:

| EEPROM Pin 8, +5V | 1 | 10 | Ground EEPROM Pins 5 and 6 |
|---|---|---|---|
| EEPROM Pin 1, Select | 2 | 9 | N/C |
| EEPROM Pin 2, Clock | 3 | 8 | Ground (key installed detection) |
| EEPROM Pin 3, Data In | 4 | 7 | N/C |
| EEPROM Pin 4, Data Out | 5 | 6 | N/C |

1.6 Sound

Each box is equipped with a speaker 55 (FIG. 5B) that is capable of providing a variety of sound. Each event is accompanied by a different sound. Five sounds are currently being used. The first tone is when the box is first turned on. This event triggers a rising tone. The second sound is when a key is first inserted into the box. This event triggers three short tones. The third sound is when a key is removed from the box. This event triggers a high and then low tone. The fourth sound is when a blank key is inserted. This sound is actually the second sound (three short beeps) spaced one second apart. The fifth sound is when a full key is detected by the box. This sound is actually the second sound (three short beeps) followed by a High then Low alarm sound. This sound repeats every second.

Although the present invention has been disclosed in the context of certain preferred embodiments, it will be understood by those skilled in the art that the present invention extends beyond the specifically disclosed embodiments to other alternative embodiments and equivalents thereof. Thus, it is intended that the scope of the present invention herein disclosed should not be limited by the particular disclosed embodiments herein, but shall be defined only by a fair reading of the claims which follow.

We claim:

1. A personal exercise tracking system for assisting a user to attain a desired exercise goal comprising:

a personal key having a memory device for storing information relevant to said user and/or said user's desired exercise goal;

a keybox associated with an exercise device for receiving said key and for reading said information relevant to said user and/or said user's desired exercise goal;

a data collector for collecting exercise data relevant to said user and/or said exercise device; and a comparator for comparing said exercise data to said user's desired exercise goal and for according points and/or other incentive rewards when said exercise data indicates that said user is exercising at an intensity level and/or duration adequate to achieve said user's desired exercise goal.

2. The personal exercise tracking system of claim 1 wherein said keybox is associated with an exercise device comprising one of the following devices: treadmill, bicycle, stationary bicycle, stair-climber, rowing machine, weight lifting or universal machine.

3. The personal exercise tracking system of claim 1 wherein each personal key has a memory device sufficient to stored said user's fitness program, desired fitness or exercise goal and progress in reaching or maintaining said fitness or exercise goal in terms of a number of said points achieved over a period of time.

4. The personal exercise tracking system of claim 3 wherein said memory device comprises a re-programmable EEPROM memory storage device.

5. The personal exercise tracking system of claim 1 wherein said comparator accords points as follows: (i) for each predetermined unit of time that the user's key is inserted in the keybox; (ii) for each predetermined unit of time the user indicates their heart rate is at a level that will allow the user to achieve their desired fitness goal; and/or (iii) for each predetermined unit of time the user's measured heart rate is at a level that will allow the user to achieve their fitness goal.

6. The personal exercise tracking system of claim 1 wherein each personal key is removable and contains all such information relevant to said user and/or said user's exercise goal and progress toward said user's exercise gaol such that users can use their personal key at any number of different facilities.

7. The personal exercise tracking system of claim 1 wherein said keybox is incorporated in the display of an associated exercise machine.

8. The personal exercise tracking system of claim 1 further comprising a data readout or print out for displaying or printing said user's exercise program, exercise goal, number of points accumulated and/or other information relevant to said user's exercise workout or fitness goal.

9. The personal exercise tracking system of claim 1 further comprising a heart rate detector for measuring the actual heart rate of said user and wherein said comparator accords said points whenever said measured heart rate is maintained above a predetermined threshold level for a predetermined period of time.

10. The personal exercise tracking system of claim 1 wherein said heart rate detector provides a 6 beat rolling average of measured heart beat.

11. The personal exercise tracking system of claim 1 wherein said heart rate detector further comprises a first filter that will not accept two heart beats if they occur too close together, a second filter to cancel variations in the users heart rate that exceed 10 BPM on two consecutive beats and a third filter to mask values outside 50 to 200 BPM reading.

12. The personal exercise tracking system of claim 1 wherein said comparator is adapted to accord incentive rewards in the form of points or an exercise score that is stored on said user's personal key or on a display readout.

13. The personal exercise tracking system of claim 1 wherein comparator is adapted to accord incentive rewards in the form of congratulatory sounds or voice recordings.

14. A method of tracking personal fitness goals comprising the steps of:

storing information on a removable key relevant to a user's exercise program and desired exercise goal;

reading said information;

collecting exercise data relevant to said user and/or an exercise device which said user is using; and comparing said exercise data to said user's desired exercise goal and for according points and/or other incentive rewards when said exercise data indicates that said user is exercising at an intensity level and/or duration adequate to achieve said user's desired exercise goal.

15. The method of claim 14 wherein said comparator accords points or other incentive rewards as follows: (i) for each predetermined unit of time that the user's key is inserted in the keybox; (ii) for each predetermined unit of time the user indicates their heart rate is at a level that will allow the user to achieve their desired fitness goal; and/or (iii) for each predetermined unit of time the user's measured heart rate is at a level that will allow the user to achieve their fitness goal.

16. The method of claim 14 wherein points or incentive rewards are accorded in the form of points or an exercise score that is stored on said user's personal key or on a display readout.

17. The method of claim 14 wherein incentive rewards are provided in the form of congratulatory sounds or voice recordings.

18. The method of claim 14 further comprising the step of displaying or printing out said user's exercise program, exercise goal, number of points accumulated and/or other information relevant to said user's exercise workout or fitness goal.

19. The method of claim 14 further comprising the step of measuring the actual heart rate of said user and according points whenever said measured heart rate is maintained above a predetermined threshold level for a predetermined period of time.

20. The method of claim 19 comprising the further step of averaging said measured rate to provide a 6 beat rolling average of measured heart beat.

* * * * *

UNITED STATES PATENT AND TRADEMARK OFFICE
CERTIFICATE OF CORRECTION

PATENT NO. : 6,077,193
DATED : June 20, 2000
INVENTOR(S) : Kirk A. Buhler and David R. Quam Page 1 of 1

It is certified that error appears in the above-identified patent and that said Letters Patent is hereby corrected as shown below:

<u>Column 7,</u>
Line 41, change "gaol" to -- goal --.

Signed and Sealed this

Thirtieth Day of April, 2002

*Attest:*

*Attesting Officer*

JAMES E. ROGAN
*Director of the United States Patent and Trademark Office*